(12) United States Patent
Bienert et al.

(10) Patent No.: US 6,350,570 B1
(45) Date of Patent: Feb. 26, 2002

(54) METHOD FOR TRANSFERRING BIOLOGICAL MATERIAL

(75) Inventors: Klaus Bienert, Gross Kreutz; Heiko Kraack, Potsdam, both of (DE)

(73) Assignee: Max-Planck Gesellschaft zur Forderung der Wissenschaften e.V., Berlin (DE)

( * ) Notice: Subject to any disclaimer, the term of this patent is extended or adjusted under 35 U.S.C. 154(b) by 0 days.

(21) Appl. No.: 09/701,446
(22) PCT Filed: May 26, 1999
(86) PCT No.: PCT/EP99/03624
  § 371 Date: Mar. 12, 2001
  § 102(e) Date: Mar. 12, 2001
(87) PCT Pub. No.: WO99/63049
  PCT Pub. Date: Dec. 9, 1999

(30) Foreign Application Priority Data

May 29, 1998 (DE) .......................................... 198 24 243

(51) Int. Cl.⁷ .............................. C12Q 3/00; C12M 1/36
(52) U.S. Cl. .......................... 435/3; 435/30; 435/285.1; 435/286.2
(58) Field of Search .......................... 435/3, 30, 285.1, 435/286.2, 455, 468, 471

(56) References Cited

U.S. PATENT DOCUMENTS

5,854,209 A * 12/1998 Jacobs, Jr. et al.
5,892,223 A *  4/1999 Karpov et al.
6,055,453 A *  4/2000 Hofmann et al.

* cited by examiner

*Primary Examiner*—James Ketter
(74) *Attorney, Agent, or Firm*—Gray Cary Ware & Friedenrich LLP; Lisa A. Haile

(57) ABSTRACT

The invention relates to a method for transferring, for instance, a biological material arranged in a given pattern, whereby the biological material is brought into contact with needles placed on the head of a robot and the biological material is transferred to a support, whereby the needles are hard metal needles fitted with a biocompatible coating. The biocompatible coating preferably consists of metal-nitrogen compounds. Preferably, an anticorrosion coating is applied underneath the biocompatible coating. Once the biological material has been arranged in a given pattern, the needles mounted on the robot head are arranged according to the same pattern. Preferably, the pattern corresponds to the pattern of the arrangement of microtitre plate wells. The invention also relates to a robot head fitted with the inventive hard metal needles. Said robot head particularly forms part of a picking and/or a spotting robot. The invention further relates to the utilization of hard metal needles fitted with a biocompatible coating for transferring, for instance, biological material arranged in a given pattern to a support.

22 Claims, 3 Drawing Sheets

METHOD FOR TRANSFERRING BIOLOGICAL MATERIAL

Figure 1:
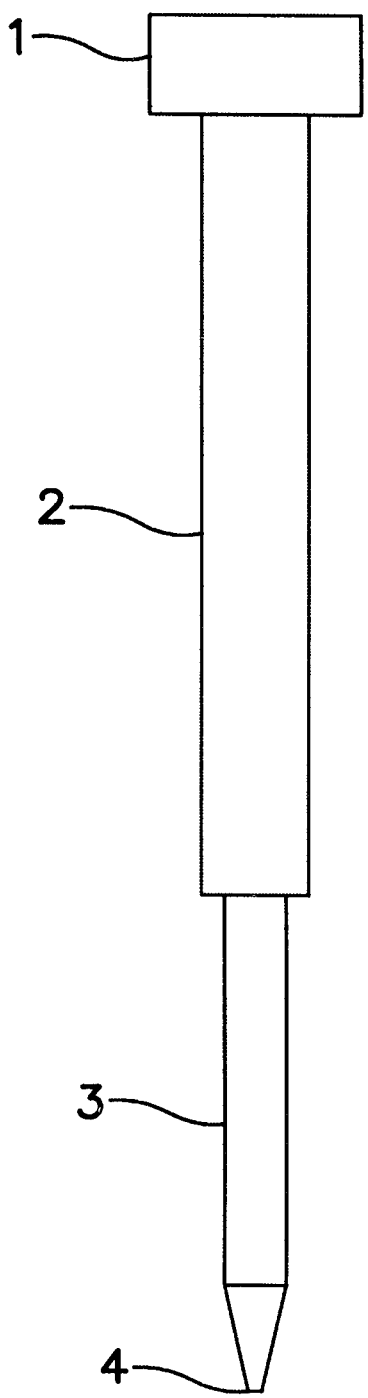

The invention relates to a method for transferring biological material arranged, for instance, in a given pattern, wherein the biological material is brought into contact with needles placed on the head of a robot and the biological material is transferred to a support, wherein the needles are hard metal needles fitted with a biocompatible coating. The biocompatible coating preferably consists of metal-nitrogen compounds. Furthermore, preferably, an anticorrosion coating is applied underneath the biocompatible coating. Once the biological material has been arranged in a given pattern, the needles mounted on the robot head are arranged according to the same pattern. Preferably, the pattern corresponds to the pattern of the arrangement of microtitre plate wells. Furthermore, the invention relates to a robot head fitted with the hard metal needles according to the invention. In particular, said robot head particularly forms part of a picking and/or a spotting robot. Finally, the invention relates to the utilization of hard metal needles fitted with a biocompatible coating for transferring, for instance, biological material arranged in a given pattern to a support.

Computer-assisted screening methods are more and more used in biologically or biochemically orientated laboratories. As example, the Human Genome Project has shown there is a need of methods and equipment for the identification and cataloguing of more and more material within shorter and shorter intervals. Robots have been developed in recent years for the screening of gene banks, which have considerably facilitated a systematic screening of the libraries and a subsequent analysis. The robots used in these methods are generally referred to as picking/spotting robots. The currently used picking/spotting robots are capable of picking up biological material and putting it down in a well-aimed way and distributing it. For this purpose, gadgets (needle templates) are used in different designs, for instance, in arrays of 8×12 or 16×24. These needle templates are fitted with high-grade steel needles. The high-grade steel needles have a good corrosion-resisting quality but a low mechanical resistance. The use of picking/spotting robots known in the art, therefore, often leads to mechanical deformations and, thus, to bad hitting results (picking) and thus to time-consuming extra work. The use of spotting needles in spotting robots leads to, for instance on high density filters, bad grids of biological material after deformation of the needles.

The problem underlying the present invention was thus to modify the method known from the prior art in a way that putting down and distribution of biological material in a well-aimed manner is guaranteed when using picking/spotting robots. Furthermore, after having been put down and distributed, the biological material should, of course, maintain its biological characteristics to an extent as large as possible.

This technical problem has been solved by providing the embodiments characterized in the claims. Thus, the invention relates to a method for transferring biological material, wherein the biological material is brought into contact with needles placed on a robot head and the biological material is transferred to a support characterized by the needles being hard metal needles fitted with a biocompatible coating.

Surprisingly, according to the invention, it was found that a method according to the above-mentioned general term renders the desired effect if the high-grade steel pins known from the prior art are replaced by hard metal needles fitted with a biocompatible coating. This measure leads to the fact that a high hitting percentage and long-term use of the used robot heads is guaranteed by the met hod of the invention. The such treated hard metal needles have proved to be corrosion-resistant and to generate a minimized friction in the gadget. They are further characterized by a high abrasion resistance and are wear-resistant. The biocompatible coating resulted in a resistance to wear which was 20 times higher than an ordinary gold coating.

By means of the method according to the invention it was possible to achieve a high accuracy concerning the picking and no mechanical deformation was observed. The modifications and deformations of the picking needle known in the prior art which lead to a deterioration of accuracy due to the change of position in the gadget no longer occur. Therefore, the problem of a computer-controlled correction which had been solved insufficiently in the prior art also becomes irrelevant. For the known correcting systems only correct errors concerning the position of the whole picking head. In the case of crooked needles, a correction by means of software was not possible. Therefore, the method according to the invention allows an optimum utilization of the camera-correction system which corrects, above all, errors concerning the position of the picking head. Due to the minimized friction described above there are altogether fewer cases of disturbance due to stuck needles. The cleaning of the picking head is also unproblematic and can, for example, be performed in water. After all, the higher stability/resistance of the needles allow a denser arrangement on the robot head.

In a preferred embodiment of the method according to the invention the biocompatible coating consists essentially or exclusively of TiN, TiCN, TiAlN or CrN. If titanium nitrite is used as a biocompatible coating, the thickness of layer is, for instance, 4 $\mu$m at 2400 HV (diamond penetrator hardness (DPH)). The titanium nitrite can, for instance, be applied by means of physical deposition in the vapor phase (PVD, Physical Vapor Deposition). Thus, titanium is vaporized by means of electric arch and, simultaneously, nitrogen is added in high vacuum. The coating temperature is normally below 500° C. while there is no structural transformation, no heat casting and no thermal stress. The wear of material is significantly minimized due to the low reactivity of titanium nitrite to ferrous materials. Due to its higher coating hardness the titanium carbon nitrite coating is a good complement to the titanium nitrite coating. It normally exhibits a hardness of 3000 HV (DPH) at a coating density of approximately 3 $\mu$m. The titanium aluminium nitrite coating is chosen because of its high hardness and oxidation resistance under the hardest operating conditions. At a thickness of up to approximately 3 mm it has normally a hardness of 3300 HV (DPH). The use of a chromium nitrate coating having a relatively high hardness in combination with a low brittleness allows for the depositing of thicker layers, too. The hardness of this kind of coated needles is approximately 2000 HV (DPH) with a thickness of layer of up to maximally 50 $\mu$m.

According to the invention mixtures of the above-mentioned biocompatible coatings are used as well.

In a further preferred embodiment of the method of the invention the hard metal needles are ejector pins or clipping punches. The needles or punches can, for instance, be of alloyed cold work steel (WS), for instance, of material having the material numbers 1.2516, 1.2210 or 1.2842 (e.g. DIN 1530/ISO 6751). When using material no. WS 1.2516 the hardness of the needle head is normally 45 HRC±2 HRC (Hardness Rockwell Cowe), whereas the pin shank of the pinpoint has a hardness of normally 60 HRC±2 HRC. In this preferred embodiment these pins are hardened. The heat-resistance is approximately 250° C. After the coating with, for instance, titanium nitrite the ejector pins have a hardness of approximately 2400 HV (DPH). The above-mentioned materials have a retention of hardness of at least 200° C. It is ductile hard tool steel with a medium resistance to wear.

Moreover, high-alloyed tool steel (HWS), for instance, material numbers 1.2601 or 1.2379 can be used. These tool steels have a high resistance to wear and a high retention of hardness. If tool steel having the material number WS 1.2379 is used, the pinpoint/the pin shank has a hardness of normally 62±2 HRC. The needle head normally has a hardness of 50±5 HRC. Moreover, high-alloyed high-speed steel (HSS), for example material number 1.3343, can be used in the method according to the invention. Such materials are characterized by highest resistance to wear, good ductility and high heat-resistance. If such steel, for example material number WS 1.3343, is used the pin shank/the pinpoint normally have a hardness of 64±2 HRC, whereas the needle head has a hardness of 50±5 HRC. Moreover, powder metallurgically-produced high-speed (ASP 23) steel is preferably used in the method according to the invention. Such materials have an excellent resistance to wear and an excellent compression resistance and, furthermore, are characterized by high ductility as well as by very good homogeneity of the material. If, for instance, such high-speed steel with material number ASP 23 is used, the pin shank/the pinpoint normally has a hardness of 64±2 HRC. The needle head normally has a hardness of 50±5 HRC.

In a further preferred embodiment of the method of the invention the robot head is the head of a picking robot.

In another embodiment of the method according to the invention the method is characterized by the biological material being arranged in a given pattern and the biological material being brought into contact with needles being mounted on a robot head according to the same pattern. This method is preferably used if the robot is a spotting robot. If this type of robot is used for the replication of the biological material, for putting it into liquid medium, the needles are referred to as replica needles, see FIG. 3.

In a further preferred embodiment of the method of the invention the robot head is therefore the head of a spotting robot. The above remarks as to the advantages of the method of the invention in the embodiment, wherein the robot head is the head of a picking robot, are correspondingly true in the case of the robot head being the head of a spotting robot.

In a further preferred embodiment of the method of the invention the pattern of the arrangement corresponds to the pattern of the wells in the microtitre plate or to the pattern of reactors arranged in a correspondingly regular pattern.

In this embodiment of the method of the invention, for instance, clones having grown in microtitre plates, for instance, from mammalian cells, can be directly transferred to a material which can be used in the screening method.

In a further preferred embodiment of the method of the invention the biological material comprises nucleic acids, (poly)peptides or transformed host organisms. A particular advantage of this embodiment is that the material used for the coating of the hard metal needles is biocompatible. Thus, the biological material can be analyzed further without having to risk losses due to inactivation or chemical degradation. In the case of transformed host organisms, for instance, the latter can be cultured again after transfer into a viable state and thus be analyzed further. Nucleic acids can be analyzed further according to standard screening methods like hybridizations. Polypeptides, for instance, can be further analyzed by means of suitable antibodies, without being subjected to procedural modifications.

In a particularly preferred embodiment of the method according to the invention the transformed host organisms are yeasts, Pistoria- or Saccharomyces-cells, bacteria, preferably *E. coli*, insect cells, preferably *Spodoptera frugiperda* cells, fungi cells, preferably Aspergillus cells, plant cells or mammalian cells.

Another preferred embodiment of the invention relates to a method wherein the support is a liquid or a solid support. Particularly preferred in this connection is that the liquid support is a culture medium, a medium for the storage of biological material, a reaction buffer or a staining solution. An example of a reaction buffer is a buffer which is used in a polymerase chain reaction (PCR). In addition to the actual buffer solution which can be produced by the person skilled in the art according to the standard methods the buffer can contain further components of organic or inorganic origin. In another preferred embodiment of the invention the solid support is a nitrocellulose membrane to which nucleic acids or (poly)peptides can be linked, a polyvidendifluoride membrane to which (poly)peptides can be linked, or a glass support, preferably for the application of (poly)peptides or nucleic acids.

Another preferred embodiment of the method of the invention is characterized by the anticorrosion coating being applied underneath the biocompatible coating. Normally the coating placed underneath is applied by means of a first coating whereas the biocompatible coating is subsequently applied onto the needle. A particular effect of the anticorrosion coating is that the needles are protected from rusting. Therefore, they give the needles improved resistance. This is particularly the case if the biocompatible coating is applied by means of evaporation. During evaporization no biocompatible coating is applied onto the suspension points of the needles. At these points additional measures against, for instance, corrosion have been taken when placing an anticorrosion coating onto the needles.

The anticorrosion coating is preferably a nickel coat or a chromium coat. A coating particularly with nickel has also the advantage that the application of this coating can be performed at low cost.

The invention also relates to a robot head, in particular for the performance of the method according to the invention, which exhibits the above-described hard metal needles fitted with a biocompatible coating. It is particularly preferred that the robot head forms part of a picking robot or a spotting robot. Finally, the invention relates to the use of the above described coated hard metal needles for transferring biological material arranged in a given pattern to a support.

The figures show:

FIG. 1 shows an embodiment of a spotting needle with needle head 1, pin shank 2, stepped pin shank 3 and pinpoint 4. In this embodiment the needle head has a length of 2.0 mm and a diameter of 4.0 mm. The measures of the pin shank are the following: length: 16.0 mm, diameter: 2.0 mm. The reduced or stepped pin shank has a length of 8.0 mm and a diameter of 1.0 mm. The pin point, finally, has a length of 2.0 mm and a diameter of 250 μm or 400 μm.

Figure 2:
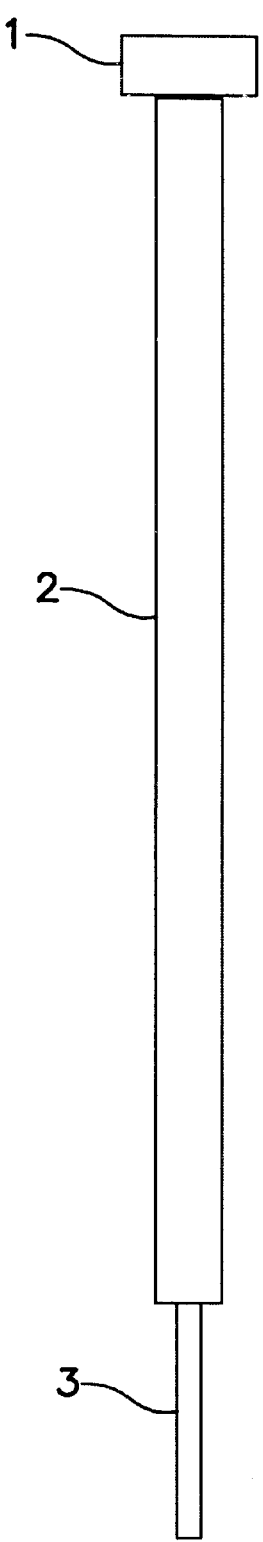

FIG. 2 shows an embodiment of a picking needle wherein needle head 1, pin shank 2 and pinpoint 3 can be seen. In this embodiment the needle head has a length of 2.0 mm and a diameter of 4.0 mm. The pin shank has a length of 40.0 mm and diameter of 2.0 mm. The pinpoint, finally, has a length of 8.0 mm and a diameter of 0.8 mm.

Figure 3:
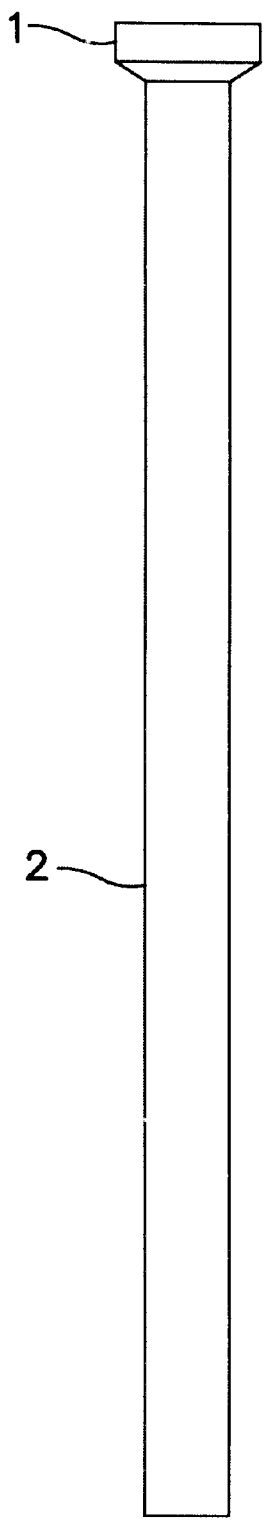

FIG. 3 shows an embodiment of a replica needle with a needle head 1 and a pin shank 2. The needle head has a length of 1.0 mm and a diameter of 2.0 mm, whereas the pin shank has length of 29.0 mm and a diameter of 1.2 mm.

The examples explain the invention.

EXAMPLE 1

Use of Hard Metal Needles Fitted with a Titanium Coating for Spotting

Transformed CHO cells are taken from microtitre plates (384 wells) by means of a gadget and transferred to nylon membranes in a high-resolution grid. The filters are prepared for hybridization according to the standard methods and hybridized with a probe which is specific for the foreign gene transferred into the CHO cells and which carry a radioactive label. The washing of the filters is followed by an analysis by means of a computer-controlled photogrammetry. In this context, the favorable events (hybridizations) are expected in the predefined grid. The tests carried out with the spotting needles known in the prior art (FIG. 1) show a higher amount of grid errors than the tests carried out with the above-described needles according to the invention. The results show that the use of spotting needles made of material known from the prior art makes the automatic analysis considerably more difficult or makes it impossible.

EXAMPLE 2

Use of Hard Metal Needles Fitted with a Titanium Coating for Picking

Robot heads fitted with needles consisting of material known from the prior art or robot heads fitted with needles being ejector pins coated with titanium nitrite. During the picking procedure transformed colonies (CHO cells) grown in culture medium are identified by means of a camera system and subsequently picked up by picking needles (FIG. 2) in order to place them into microtitre plates in an arranged way. In this context, the needles known from the prior art lead to worse results. For instance, the colonies were only touched and thus less material was transferred. In individual cases, needles known from the prior art even missed colonies totally which also leads to a suboptimal result. With regard to the picking needles described in connection with this invention, however, no deformations and therefore no errors were observed over a relatively long period of time (4 months), while the material was sorted and put down.

EXAMPLE 3

Use of Hard Metal Needles with Titanium Coating for Spotting of PCR Products The nucleic acids of a pancreas cDNA gene bank synthesized by means of a polymerase chain reaction (PCR) using vector specific primers according to standard methods in a microtitre plate (384 wells) are removed by means of a gadget and applied onto a glass support arranged as dense as possible (see below). By means of hybridization with suitable insulin-specific probes marked via non-radioactive methods (fluorescent dye) according to standard methods, the expression of the insulin gene represented by a PCR product in pancreas tissue could be determined and quantified. The analysis of these so-called microarrays was carried out by a computer-assisted photogrammetry. For this purpose, adherence to the spotting pattern, which should be reproducible, was necessary in an as exact as possible way, which can only be achieved by means of the needles described in this invention.

In order to be able to analyze an as large as possible amount of genes at the same time an arrangement of the PCR products as dense as possible on the glass support is desirable. If the PCR products are applied by spotting, this dense arrangement is limited by the thickness of the needles. The latter can be further reduced by means of the method for stiffening the spotting needles described according to the invention.

With a diameter of the pinpoint of 50 $\mu$m it was thus possible to arrange the spots 50 $\mu$m apart from each other. With such small gaps, the smallest deformations can as can be seen in the prior art, result in grids which are difficult to analyze or which cannot be analyzed at all.

Thus the needles described in this invention allow for the routine application of PCR products in larger batches on glass supports by means of spotting with the density and exactness required in the course of modern detection methods.

What is claimed is:

1. A method for transferring a biological material, wherein the biological material is brought into contact with needles placed on the head of a robot and the biological material is transferred to a support, characterized in that the needles are hard metal needles fitted with a biocompatible coating consisting of metal-nitrogen compounds.

2. The method of claim 1, wherein the biocompatible coating consists essentially of titanium nitride, TiCN, TiAlN or CrN or a mixture thereof.

3. The method of claim 1, wherein the hard metal needles are ejector pins or clipping punches.

4. The method of claim 1, wherein the robot head is the head of a picking robot.

5. The method of claim 1, wherein the biological material is arranged in a pattern and wherein the biological material is brought into contact with needles placed on a robot head according to the same pattern.

6. The method of claim 1, wherein the robot head is a head of a spotting robot.

7. The method of claim 5, wherein the pattern corresponds to a pattern of wells of a microtitre plate or a pattern of reaction tubes arranged in a pattern.

8. The method of claim 1, wherein the biological material comprises nucleic acids, peptides, polypeptides or transformed host organisms.

9. The method of claim 8, wherein the transformed host organisms are yeast cells, bacteria, insect cells, fungus cells, plant cells or mammalian cells.

10. The method of claim 9, wherein the yeast cells are Pistoria cells or Saccharomyces cells.

11. The method of claim 9, wherein the bacteria are *E. coli*.

12. The method of claim 9, wherein the insect cells are *Spodoptera frugiperda* cells.

13. The method of claim 9, wherein the fungus cells are Aspergillus cells.

14. The method of claim 1, wherein the support is a liquid support or a solid support.

15. The method of claim 14, wherein the liquid support is a culture medium, a medium for storage of biological material, a reaction buffer or a staining solution.

16. The method of claim 14, wherein the solid support is a nitrocellulose membrane, a polyvidendi fluoride membrane or a glass support.

17. The method of claim 1, wherein an anticorrosion coating is applied underneath the biocompatible coating.

18. The method of claim 17, wherein the anticorrosion coating is a nickel coating or a chromium coating.

19. A robot head, comprising hard metal needles having a biocompatible coating.

20. The robot head of claim 19, wherein the robot head comprises a picking robot or a spotting robot.

21. A method of using hard metal needles with a biocompatible coating for transferring biological material to a support, comprising contacting the biological material with the hard metal needles and transferring the biological material to the support.

22. The method of claim 21, wherein the biological material is arranged in a pattern.

* * * * *